US00PP09480P

United States Patent [19]

Challet

[11] Patent Number: Plant 9,480

[45] Date of Patent: Mar. 19, 1996

[54] CHRYSANTHEMUM PLANT NAMED 'CHATUPA'

[75] Inventor: Jean-Pierre Challet, Lafayette, Calif.

[73] Assignee: Selection New Plant Sarl, Le Cannet Des Maures, France

[21] Appl. No.: 273,997

[22] Filed: Jul. 12, 1994

[51] Int. Cl.[6] ..... A01H 5/00

[52] U.S. Cl. ..... Plt./79

[58] Field of Search ..... Plt./76, 79, 78

[56] References Cited

U.S. PATENT DOCUMENTS

| | | | |
|---|---|---|---|
| P.P. 2,520 | 5/1965 | Dunham | Plt./79 |
| P.P. 3,194 | 5/1972 | Shoesmith | Plt./79 |
| P.P. 3,409 | 11/1973 | Jessel, Jr. et al. | Plt./79 |
| P.P. 3,481 | 2/1974 | Jessel, Jr. et al. | Plt./79 |
| P.P. 4,122 | 10/1977 | Jessel, Jr. et al. | Plt./79 |
| P.P. 5,061 | 6/1983 | Hartman | Plt./79 |
| P.P. 5,088 | 8/1983 | Shoesmith | Plt./79 |
| P.P. 7,389 | 12/1990 | VandenBerg | Plt./79 |
| 4,616,099 | 10/1986 | Sparkes | 47/58 |

OTHER PUBLICATIONS

Datta, 1991, "Evaluation of recurrent irradiation on vegetatively propagated ornamentals: Chrysanthemum", J. Nuclear Agric. Biol., 20(2):81–86.

Banerji et al., 1990, "Induction of somatic mutation in chrysanthemum cultivar 'Anupam'", J. Nuclear Agric. Biol, vol. 19, pp. 252–256.

Das, et al., 1977, "Improvement of some vegetatively propagated ornamentals by gamma radiation", Indian J. Hart. 34(2): 169–174.

Gupta, et al., 1977, "Mutation breeding of chrysanthemum. II. Detection of gamma ray induced mutation in vM2." J. Nuclear Agric. Biol. 7(2):50–54.

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Chan, 1966, "Chrysanthemum and rose mutations induced by Xrays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using X–and gamma radiation", Euphytica, 15:204–210.

*Primary Examiner*—Howard J. Locker

*Attorney, Agent, or Firm*—Burns, Doane, Swecker & Mathis

[57] ABSTRACT

A new and distinct Chrysanthemum cultivar named 'Chatupa' is provided. The new cultivar is a mutation of the 'Chalecat' cultivar (U.S. Plant patent application Ser. No. 08/273,998, filed Jul. 12, 1994). Attractive extremely large double incurved blossoms of the pompon type are formed that are honey gold in coloration. The blossoms are long lasting and commonly keep their form for approximately three weeks on the plant and more than four weeks in a vase. The response period of the flowers is approximately nine weeks. Recurrent profuse flower production throughout the year is possible. The plant possesses strong thin stems, forms dark green glossy leaves, and commonly assumes a height of approximately 45 to 50 cm. The light blossom coloration contrasts nicely with the dark green foliage. The new cultivar is particularly suited for use in the production of a decorative pot Chrysanthemum that grows well disbudded. No growth regulator is necessary to achieve the short to medium plant height.

4 Drawing Sheets

SUMMARY OF THE INVENTION

The present invention comprises a new and distinct cultivar of Chrysanthemum, botanically known as *Dendranthema grandiflora*, and hereinafter is referred to by the cultivar name 'Chatupa'.

The new cultivar of the present invention was created through the gamma irradiation of the 'Chalecat' cultivar (U.S. Plant patent application Ser. No. 08/273,988, filed Jul. 12, 1994). The parent 'Chalecat' cultivar was formed by the crossing of the 'Siky' cultivar (non-patented in the United States) and the 'Prouesse' cultivar (non-patented in the United States) as described in my copending U.S. Plant patent application.

During June 1980, at Saint Paul Lez Durance, France, groups of 1,000 rooted cuttings of the 'Chalecat' cultivar having an age of two weeks were irradiated with gamma rays through the packing boxes at rates of 1.8, 2.5 and 3.0Krads. Following irradiation the plants were shipped to Nuaille, Trementines, France, and planted in 4 liter pots, pinched, and grown outside until September, next grown in greenhouse, were not disbudded, and were carefully observed. It was found that most of the plants irradiated at a rate of 3.0 Krads died. Those plants that were irradiated at a rate of 2.5 Krads exhibited no growth following pinching and were discarded. Many different mutations were observed in the plants that were irradiated at a rate of 1.8 Krads. A single mutation that exhibits the characteristics of the 'Chatupa' cultivar was discovered among these plants. Also, a single mutuation that exhibits the characteristics of the 'Chahaul' cultivar (U.S. Plant patent application Ser. No. 08/273,996, filed Jul. 12, 1994) and a single mutation of the 'Chalurido' cultivar (U.S. Plant patent application Ser. No. 08/273,999, filed Jul. 12, 1994) were discovered among the same group of plants. It would have been immpossible for a plant scientist to have predicted in advance that new cultivars having the combination of characteristics of the presently claimed 'Chatupa' cultivar and the sister 'Chahaul' and 'Chalurido' cultivars could have been formed even if the parent 'Chalecat' cultivar would have been available for such experimentation.

It was found that the new cultivar of the present invention:

(a) exhibits attractive extremely large double incurved pompon blossoms that are honey gold in coloration,
(b) exhibits a flower response period of approximately nine weeks,
(c) forms attractive dark green glossy foliage,
(d) achieves a short to medium plant height, and
(e) is particularly suited for pot mum production on a recurrent basis throughout the year.

The new cultivar is intended primarily as a decorative pot Chrysanthemum for growing indoors. However, it also can be grown for cut flower production in those instances where stems of approximately 40 cm. are acceptable. Also, the new cultivar can be grown outdoors at temperatures above freezing.

The new cultivar is particularly suited for disbudded growth. An increased mumber of branches readily can be induced by pinching. The pinching of a cutting commonly produces approximately 3 to 4 stems per cutting. No growth regulator is required to produce the short to medium plant height; however, a growth regulator optionally can be utilized.

The new cultivar can be considered to be an October-flowering greenhouse variety with the natural flowering season commonly occurring in weeks 42 and 43 of the year. Attractive blossoms can be produced on a recurrent basis throughout the year with the indicated nine week response period. The blossoms are long lasting and commonly can be maintained on the plant for approximately three weeks, and commonly exhibit a vase life of more than four weeks.

Asexual reproduction of the new cultivar by cuttings initially taken during 1989, as performed in Nuaille, Trementines, France, in a controlled environment has demonstrated that the characteristics of the new cultivar as herein described are firmly fixed and are retained through successive generations of asexual propagation.

'Chatupa' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chatupa' cultivar of the present invention exhibits a combination of characteristics that readily distinguish it from the parent 'Chalecat' cultivar. For instance, the 'Chatupa' cultivar exhibits a honey gold capitulum unlike the 'Chalecat' cultivar, the 'Chatupa' cultivar generally exhibits a larger capitulum than the 'Chalecat' cultivar, a foliage coloration Green Group 137A unlike the Yellow-Green Group 147A coloration of the 'Chalecat' cultivar, an angular stem cross section unlike the round cross section of the 'Chalecat' cultivar, a stem coloration between Yellow-Green Group 144A and 144B unlike the stem coloration of Yellow-Green Group 146B of the 'Chalecat' cultivar, a medium leaf serration unlike the medium to fine serration of the 'Chalecat' cultivar, a cuspidate leaf apex unlike the acuminate leaf apex of the 'Chalecat' cultivar, and a claw at the base of the sinus between lateral leaf lobes unlike the 'Chalecat' cultivar.

As indicated, other mutations of the 'Chalecat' cultivar are the 'Chahalu' cultivar and the 'Chalurido' cultivar. Each of these additional cultivars can be readily distinguished from the parent 'Chalecat' cultivar with respect to a number of plant characteristics.

The 'Chahalu' cultivar exhibits a lemon yellow capitulum unlike the 'Chatupa' cultivar, commonly forms a generally smaller capitulum than the 'Chatupa' cultivar, a foliage coloration between Green Group 137A and 139A unlike the coloration Green Group 137A of the 'Chatupa' cultivar, a stem coloration Yellow-Green Group 144A unlike the coloration between Yellow-Green Group 144A and 144B of the 'Chatupa' cultivar, course leaf serration unlike the medium leaf serration of the 'Chatupa' cultivar, an acute leaf base shape unlike the rounded tending to cordate base of the 'Chatupa' cultivar, a cuspidate leaf apex unlike the acuminate leaf apex of the 'Chatupa' cultivar, and a diverging margin of sinus between lateral leaf lobes unlike the converging margin of the 'Chaptupa' cultivar.

The 'Chalurido' cultivar exhibits a capitulum having inner surfaces of Venetian violet and silvery lavender outer surfaces unlike the 'Chatupa' cultivar, commonly forms a fully opened capitulum having a generally smaller diameter than the 'Chatupa' cultivar, a foliage coloration of Yellow-Green Group 147A unlike the foliage coloration of Green Group 137A for the 'Chatupa' cultivar, a more variable fine to coarse leaf serration than the medium serration of the 'Chatupa' cultivar, approximately 37 to 40 leaves per typical stem in a long day crop before the bud opens unlike the lesser number of approximately 29 to 32 for the 'Chatupa' cultivar, a variable converging margin of sinus between lateral lobes unlike the converging margin of the 'Chatupa' cultivar, a mucronate leaf apex unlike the cuspidate leaf apex of the 'Chatupa' cultivar, and a generally asymmetric leaf base unlike the rounded tending to cordate base of the 'Chatupa' cultivar.

The new 'Chatupa' cultivar is being marketed under the GOLDEN CYMBAL trademark.

BREIF DESCRIPTION OF THE PHOTOGRAPHS

The accompanying photographs were prepared during June, 1994, and show as nearly true as it is resonably possible to make the same in color illustrations of this character, typical plants and plant parts of the new cultivar of the present invention. The plants were 12 weeks of age and were grown at Nuaille, Trementines, France, under standard greenhouse conditions which approximate those commonly utilized for the production of decorative pot mums. The plant had been disbudded in order to encourage the formation of one large bloom per stem. There had been one application of Alar growth regulant at a concentration of 3 grams per liter. Any labels in the photographs are 2.5 cm. in width can be used for size comparisons.

Figure 1:
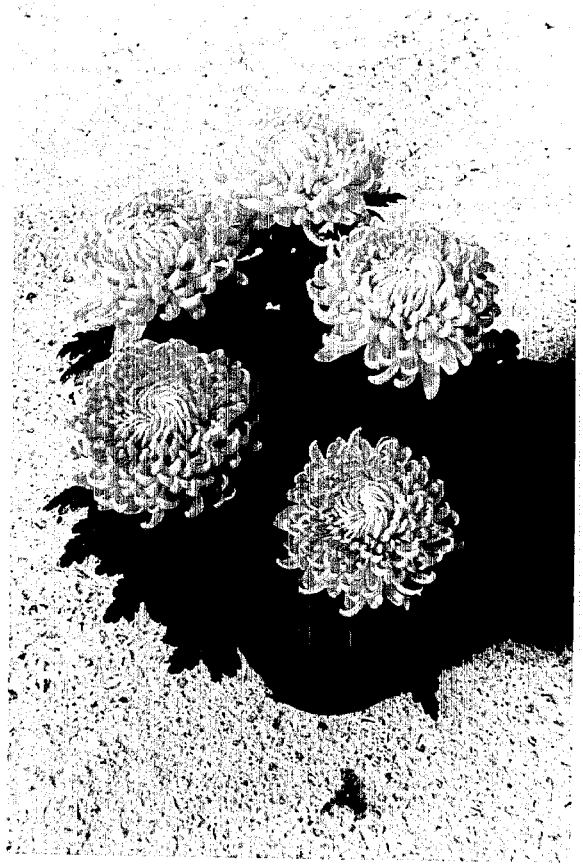
FIG. 1 illustrates typical specimens of the overall plant wherein five cuttings were placed in a 20 cm. pot. The large incurved honey gold blossoms generally in the form of large round balls, as well as the foliage, are apparent.
Figure 2:
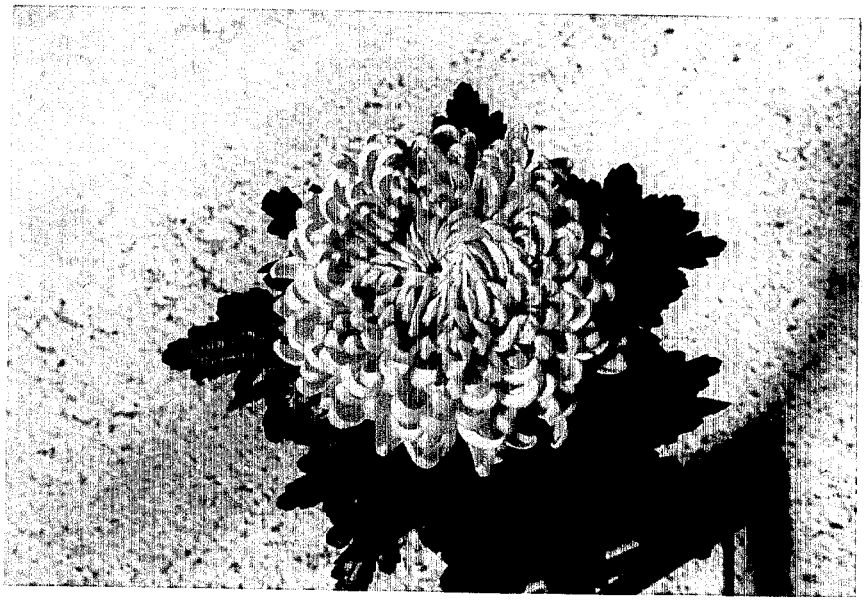
FIG. 2 illustrates a closer view of a typical flower.
Figure 3:
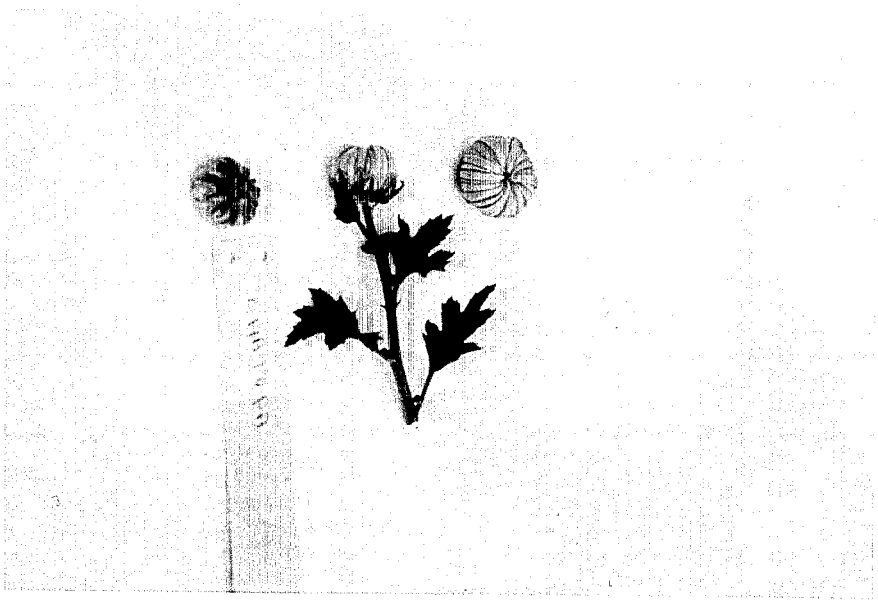
FIG. 3 illustrates from left to right, under, side, and upper views of largely unopened buds. Some tinges of red are visible at the bud stage.
Figure 4:
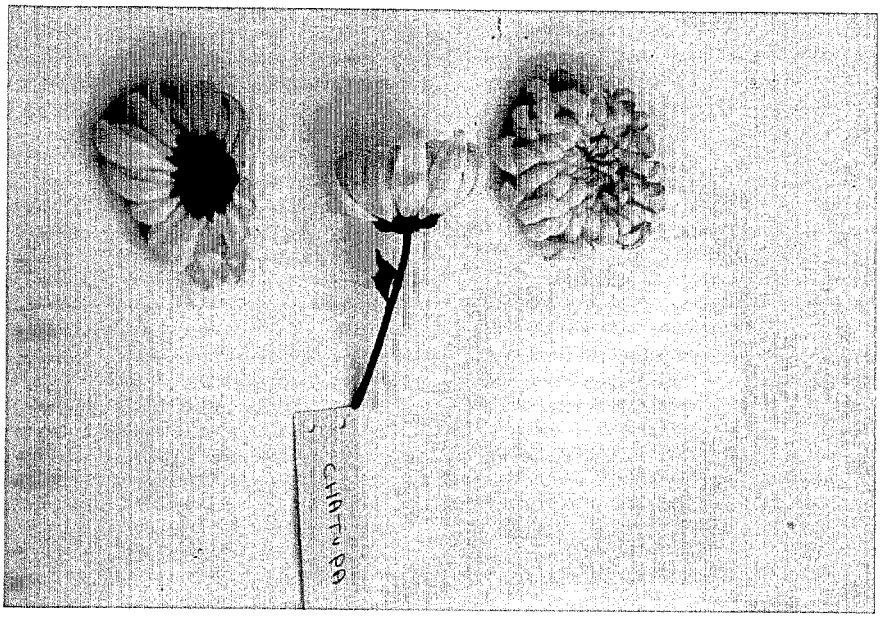

FIG. 4 illustrates from left to right, under, side, and upper views of buds in the course of opening. Tinges of red on the outer petals generally are no longer visible. Such redness commonly would be exhibited during the natural flowering season.

Figure 5:
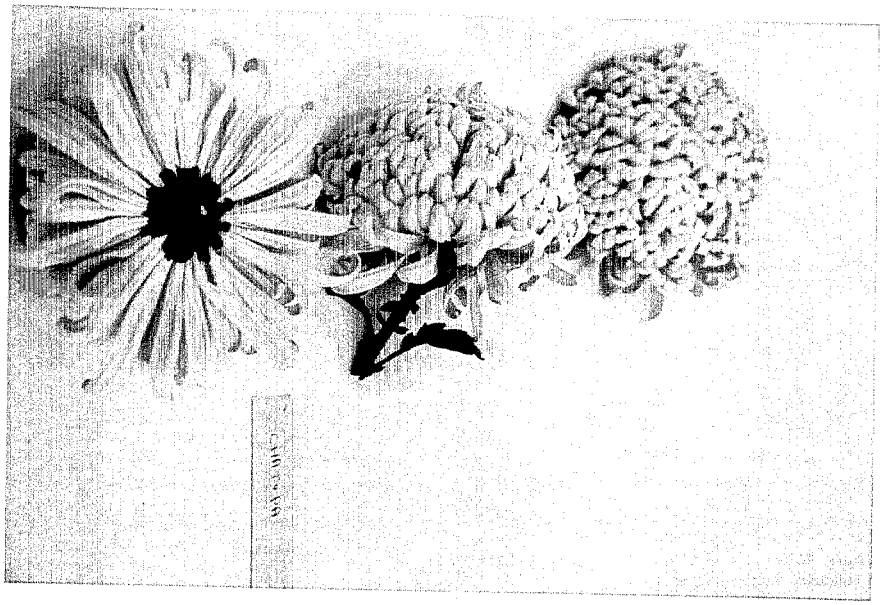

FIG. 5 illustrates from left to right, under, side, and upper views of blossoms in a more advanced stage of opening. Tinges of red on the outer petals generally are no longer visible. Such redness commonly would be exhibited during the natural flowering season.

Figure 6:
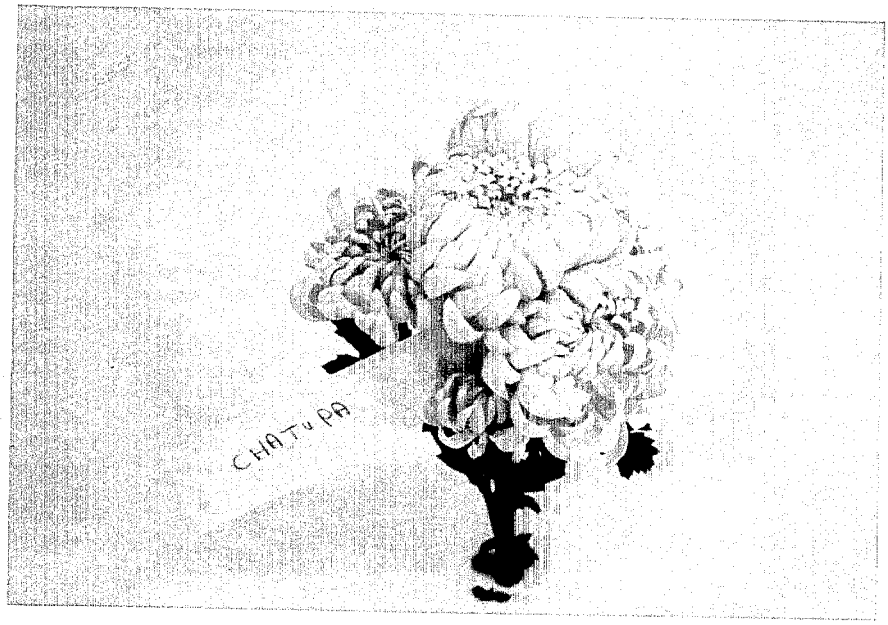

FIG. 6 illustrates a cluster or spray of blossoms.

Figure 7:
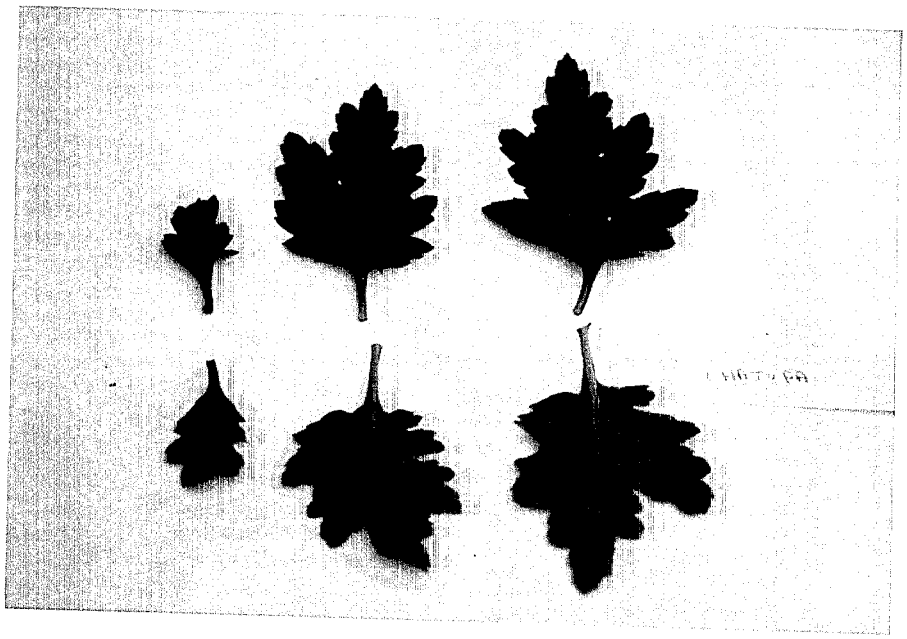

FIG. 7 illustrates at the top row, the upper surfaces of typical leaves of various sizes, and at the bottom row the under surfaces of typical leaves of various sizes.

DETAILED DESCRIPTION

The chart used in the identification of colors described hereafter is the R.H.S. Colour Chart of The Royal Horticultural Society, London, England. In some instances more common color terms are provided and are to be accorded their usual dictionary significance. The plants described were 12 weeks of age and were grown at Nuaille, Trementines, France, under standard greenhouse conditions which approximate those commonly utilized for the production of decorative pot mums.

Classification:

*Botanical.*—*Dendranthema grandiflora,* cv. 'Chatupa'.

*Commercial.*—Decorative pot mum.

Inflorescence

A. Capitulum:

*Form.*—Extremely large, double, and incurved.

*Type.*—Pompon.

*Diameter across face.*—Approximately 17 cm. on average when fully expanded.

*Frequency.*—Corymbiform, and blossoms form in profusion (as illustrated). Night temperatures above 23° C. will delay flowering. Night temperatures as low as 14° C. generally can be tolerated, and even night temperatures as low as 5° to 10° C. can be tolerated during the bud opening stage.

B. Corolla of ray and disc florets:

*Color of bud.*—Greyed-Yellow Group 162B and streaked with Greyed-Purple Group 185B on the outside.

*Disc florets.*—Tubular, yellow in coloration, few in number, very difficult to observe, and tend to be scattered among the ray florets with a small cluster at the apex of the receptacle that is visible only when the ray florets are removed.

*General tonality.*—Honey gold.

*Color ray florets.*—On the inner surfaces Yellow Group 5A and lightly overlaid with near Red Group 42B between the ribs. The outside surfaces of the florets are generally Yellow Group 6C and lightly tinged with red, Red Group 42B between the ribs. The red coloration is more prominent during the natural flowering season in the fall. Also, the overall blossom coloration commonly is brighter during the fall. As the blossoms mature the ray florets tend to take on a more brownish coloration.

*Configuration ray petals.*—Concave in cross section usually with two keels, textured, and posses pointed tips.

C. Reproductive organs:

*Androecium.*—Generally present with disc florets and absent in ray florets.

*Gynoecium.*—Generally present with most disc florest and with most ray florets.

*Pollen.*—Formed in a slight quantity and golden-yellow in coloration.

*Fragrance.*—Typical of Chrysanthemum.

Plant

A. General apperance:

*Height.*—Short to medium, and approximately 45 to 50 cm. in height on average.

B. Foliage:

*Color (upper surface).*—Green Group 137A.

*Color (under surface).*—Slightly lighter green and commonly between Green Group 137B and 137C (as illustrated).

*Long day leaf count.*—Approximately 29 to 32 leaves per typical stem in a long day crop before the bud occurs.

*Configuration.*—Lobed (as illustrated).

*Texture.*—Fleshy.

*Serration.*—Medium coarseness.

*Internode length.*—Very short.

*Stems.*—Strong, angular in cross section, between Yellow-Green Group 144A and 144B in coloration, and commonly with anthocyanin coloration at the base.

*Apex.*—Cuspidate.

*Base.*—Rounded tending to cordate.

*Claw in base of sinus between lateral lobes.*—Present.

*Margins of sinus between lateral lobes.*—Converging.

I claim:

1. A new and distinct cultivar of Chrysanthemum plant named 'Chatupa', substantially as herein shown and described, which (a) exhibits attractive extremely large double incurved pompon blossoms that are honey gold in coloration, (b) exhibits a flower response period of approximately nine weeks, (c) forms attractive dark green glossy foliage, (d) achieves a short to medium plant height, and (e) is particularly suited for pot mum production on a recurrent basis throughout the year.

* * * * *